United States Patent
Singh et al.

(10) Patent No.: US 9,027,404 B2
(45) Date of Patent: May 12, 2015

(54) ULTRASONIC NON-DESTRUCTIVE EVALUATION METHODS FOR FRICTION-WELDED BLISKS

(75) Inventors: Surendra Singh, Gilbert, AZ (US); Frederick William Vensel, Gold Canyon, AZ (US); Robert John Hogan, Chandler, AZ (US); Vincent Chung, Tempe, AZ (US)

(73) Assignee: Honeywell International Inc., Morristown, NJ (US)

( * ) Notice: Subject to any disclaimer, the term of this patent is extended or adjusted under 35 U.S.C. 154(b) by 425 days.

(21) Appl. No.: 13/473,853

(22) Filed: May 17, 2012

(65) Prior Publication Data
US 2013/0308419 A1 Nov. 21, 2013

(51) Int. Cl.
*G01N 29/04* (2006.01)
*G01N 29/44* (2006.01)
*G01N 29/26* (2006.01)
*G01N 29/06* (2006.01)

(52) U.S. Cl.
CPC ............ *G01N 29/043* (2013.01); *G01N 29/069* (2013.01); *G01N 29/262* (2013.01); *G01N 29/4436* (2013.01); *G01N 2291/2693* (2013.01)

(58) Field of Classification Search
CPC ............ G01N 29/043; G01N 29/4436; G01N 29/069; G01N 29/262
USPC ........................ 73/618, 623, 626, 602; 702/39
See application file for complete search history.

(56) References Cited

U.S. PATENT DOCUMENTS

| 3,858,439 A | | 1/1975 | Nakamura |
| 3,919,883 A | | 11/1975 | Nakamura et al. |
| 4,024,522 A | | 5/1977 | Clark et al. |
| 4,213,183 A | * | 7/1980 | Barron et al. ............. 702/39 |
| 4,289,030 A | | 9/1981 | Alers et al. |
| 4,694,699 A | | 9/1987 | Cheeke |
| 5,406,849 A | * | 4/1995 | Drescher-Krasicka et al. 73/588 |
| 5,474,225 A | | 12/1995 | Geier et al. |
| 5,760,904 A | | 6/1998 | Lorraine et al. |
| 5,915,277 A | | 6/1999 | Patton |
| 6,137,853 A | | 10/2000 | Duckering et al. |

(Continued)

FOREIGN PATENT DOCUMENTS

JP  2009282042 A  12/2009

OTHER PUBLICATIONS

Nageswaran, C. et al.; Improving phased array ultrasonic testing using models to overcome austenitic weld distortion.

(Continued)

*Primary Examiner* — J M Saint Surin
(74) *Attorney, Agent, or Firm* — Ingrassia Fisher & Lorenz, P.C.

(57) ABSTRACT

The disclosed embodiments generally relate to non-destructive evaluation methods. More particularly, the disclosed embodiments relate to ultrasonic non-destructive evaluation methods for the evaluation of friction welded bladed discs ("blisks"). In an embodiment, a method for non-destructive evaluation of a bladed disc structure includes identifying a region of interest on the bladed disc structure; positioning an ultrasonic transducer and receiver in the region of interest; scanning the region of interest using the ultrasonic transducer and receiver to produce a scan image; and comparing the scan image against a reference image to determine the presence of an anomaly in the region of interest.

10 Claims, 10 Drawing Sheets

(56) References Cited

U.S. PATENT DOCUMENTS

| | | |
|---|---|---|
| 6,719,184 B2 | 4/2004 | Ishida et al. |
| 6,736,011 B2 * | 5/2004 | Zayicek et al. ............... 73/628 |
| 6,857,553 B1 | 2/2005 | Hartman et al. |
| 6,862,936 B2 | 3/2005 | Kenderian et al. |
| 6,938,457 B2 | 9/2005 | Johnson et al. |
| 7,040,170 B2 * | 5/2006 | Tokunaga et al. ............ 73/620 |
| 7,174,788 B2 * | 2/2007 | Czerw et al. ................. 73/620 |
| 7,206,709 B2 | 4/2007 | Griffin et al. |
| 7,500,396 B2 * | 3/2009 | Bentzel ....................... 73/628 |
| 7,516,022 B2 | 4/2009 | Lee et al. |
| 7,617,733 B2 | 11/2009 | Deemer et al. |
| 7,654,143 B2 * | 2/2010 | Roney et al. ................. 73/620 |
| 7,683,894 B2 | 3/2010 | Kent |
| 7,921,575 B2 | 4/2011 | Little et al. |
| 7,966,860 B2 | 6/2011 | Dijkstra |
| 8,365,584 B1 * | 2/2013 | Quinones et al. ......... 73/112.05 |
| 8,438,929 B2 * | 5/2013 | Metala et al. ................ 73/660 |
| 8,525,831 B2 * | 9/2013 | Zhang et al. ................ 345/420 |
| 2005/0017713 A1 | 1/2005 | Goldfine et al. |
| 2005/0241397 A1 * | 11/2005 | Bergman ...................... 73/606 |
| 2008/0149687 A1 | 6/2008 | Garnett et al. |
| 2009/0185908 A1 | 7/2009 | Chung et al. |

OTHER PUBLICATIONS

Moles, M.; Entering a new phase in weld inspection; thefabricator.com, Oct. 3, 2006.

Phased Array Ultrasonic Testing (PAUT) PAUT for Weld Inspections; NDE Associated, Inc.—Ultrasonic Testing—Phased Array, Feb. 22, 2012.

Birring, A.S.; Ultrasonic phased arrays for weld testing; Replacement article for Materials Evaluation, vol. 66, No. 3, pp. 282-284, The American Society for Nondestructive Testing, Inc.

* cited by examiner

ULTRASONIC NON-DESTRUCTIVE EVALUATION METHODS FOR FRICTION-WELDED BLISKS

TECHNICAL FIELD

The disclosed embodiments generally relate to non-destructive evaluation (NDE) methods for volumetric, subsurface, and surface inspection. More particularly, the disclosed embodiments relate to ultrasonic NDE methods for the evaluation of friction welded bladed discs ("blisks").

BACKGROUND

Turbine engines are used as the primary power source for many types of aircrafts. The engines are also auxiliary power sources that drive air compressors, hydraulic pumps, and industrial gas turbine (IGT) power generation. Further, the power from turbine engines is used for stationary power supplies such as backup electrical generators for hospitals and the like.

Most turbine engines generally follow the same basic power generation procedure. Compressed air generated by axial and/or radial compressors is mixed with fuel and burned, and the expanding hot combustion gases are directed against stationary turbine vanes in the engine. The vanes turn the high velocity gas flow partially sideways to impinge on the turbine blades mounted on a rotatable turbine disk. The force of the impinging gas causes the turbine disk to spin at high speed. Jet propulsion engines use the power created by the rotating turbine disk to draw more air into the engine and the high velocity combustion gas is passed out of the gas turbine aft end to create forward thrust. Other engines use this power to turn one or more propellers, fans, electrical generators, or other devices.

Fan, low, and high pressure compressor (LPC/HPC) components are primary components in the cold section for any turbine engine and typically include complex shapes. Bladed discs ("Blisks") for example have airfoils, or blades, with surface curvature that extends in three dimensions. Blisk is the term used in the aeronautical field for a unitary piece with a rotor and airfoils. A blisk, for example, contains a series of airfoils that radiate out from a central hub. Blisks are being increasingly specified in modern turbine engine design as a method to achieve high compression in relatively short lateral spaces. These components are typically fabricated and repaired by joining separately formed blades to a disc or hub. It is desirable to optimize the design of these components during the build process. In addition, the fan/LPC/HPC components may be subject to stress loadings during turbine engine operation, and may also be impacted by foreign objects such as sand, dirt, and other such debris. Accordingly, the fan/LPC/HPC components can degrade over time due to wear, erosion and foreign object impact. Sometimes LPC/HPC components are degraded to a point at which they must be repaired or replaced, which that result in significant operating expense and time out of service.

There are several traditional methods for fabricating and repairing worn turbine engine components such as blisks, and each method has some limitations in terms of success. For example, friction welding can be used to join the blades to the disc or hub. Friction welding is achieved by moving either one or both of the blades and disc relative to one another with sufficient force to generate frictional heat, thereby joining the blade to the disc. Many times a stub is formed upstanding about a periphery of the disc for attachment of the blade. The joining stub typically follows the axial curve of the disc or hub and includes a joining surface that also follows the axial curve of the disc or hub. In other instances, friction welding is used to join the blades to the disc by providing a slot that follows the axial contour of the disk as adjoining surface.

The geometry of turbine engine blisks makes them particularly vulnerable to inadequate joining of the blades and disc due to insufficient stiffness that is achieved during the above-described welding processes. Accordingly, it is often important to establish and/or verify the structural integrity thereof. Loss of structural integrity in an object can be caused by material defects.

Non-Destructive Evaluation (NDE) methods refer to a class of methods that can be used to inspect objects for defects. NDE methods are often used to inspect materials for defects, such as structural anomalies, inclusions, cracks, etc. However, many conventional NDE methods often provide incomplete or otherwise inadequate inspections. This is especially true in difficult geometries, such as in the friction welded blisks noted above.

It would therefore be desirable to provide improved NDE methods for use with friction welded blisks to detect material defects therein. Furthermore, other desirable features and characteristics of the present invention will become apparent from the subsequent detailed description of the invention and the appended claims, taken in conjunction with the accompanying drawings and this background of the invention.

BRIEF SUMMARY

The disclosed embodiments generally relate to non-destructive evaluation (NDE) methods. More particularly, the disclosed embodiments relate to ultrasonic NDE methods for the evaluation of friction welded bladed discs ("blisks"). In an embodiment, a method for non-destructive evaluation of a bladed disc structure includes identifying a region of interest on the bladed disc structure; positioning an ultrasonic transducer and receiver in the region of interest; scanning the region of interest using the ultrasonic transducer and receiver to produce a scan image; and comparing the scan image against a reference image to determine the presence of an anomaly in the region of interest.

In another embodiment, a method for non-destructive evaluation of a bladed disc structure includes identifying a region of interest on the bladed disc structure; positioning an automated moving ultrasonic transducer and receiver in the region of interest; and scanning the region of interest using the moving ultrasonic transducer and receiver to produce a scan image. Scanning the region of interest using the ultrasonic transducer and receiver includes generating and detecting an ultrasonic wave from the moving ultrasonic transducer and receiver.

In yet another embodiment, a method for non-destructive evaluation of a bladed disc structure with finished airfoils thereon includes identifying a region of interest on the bladed disc structure with finished airfoils; scanning the region of interest using a phased-array ultrasonic (PAUT) transducer and receiver to produce a scan image; and comparing the scan image against a reference image to determine the presence of an anomaly in the region of interest.

In a variation of this embodiment, scanning the region of interest may be accomplished using electromagnetic acoustic transducers (EMATs) using transmitters and receivers to produce the scan image.

In yet another variation of this embodiment, scanning the region of interest may be accomplished using LASER Assisted Ultrasonic (LAUT) techniques using an appropriate LASER source as a transmitter and air-coupled PZT or optical sensors as receivers to produce the scan image.

In still another variation of this embodiment, scanning the region of interest may be accomplished using a non-linear ultrasonic driver and using several receivers for receiving several multiple harmonics for analyzing structural integrity, and producing a scan image thereby.

In still another variation of this embodiment, the method may further include, with regard to any of the above scanning modalities, identifying the interfaces joining the blades and the disk, and a grain size distribution in the region of interest.

For example, in one embodiment, EMAT and LAUT can be used for welding process monitoring during a linear friction welding process to identify any process introduced anomalies.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

The present invention will hereinafter be described in conjunction with the following drawing figures, wherein like numerals denote like elements, and wherein.

DETAILED DESCRIPTION

Figure 1:
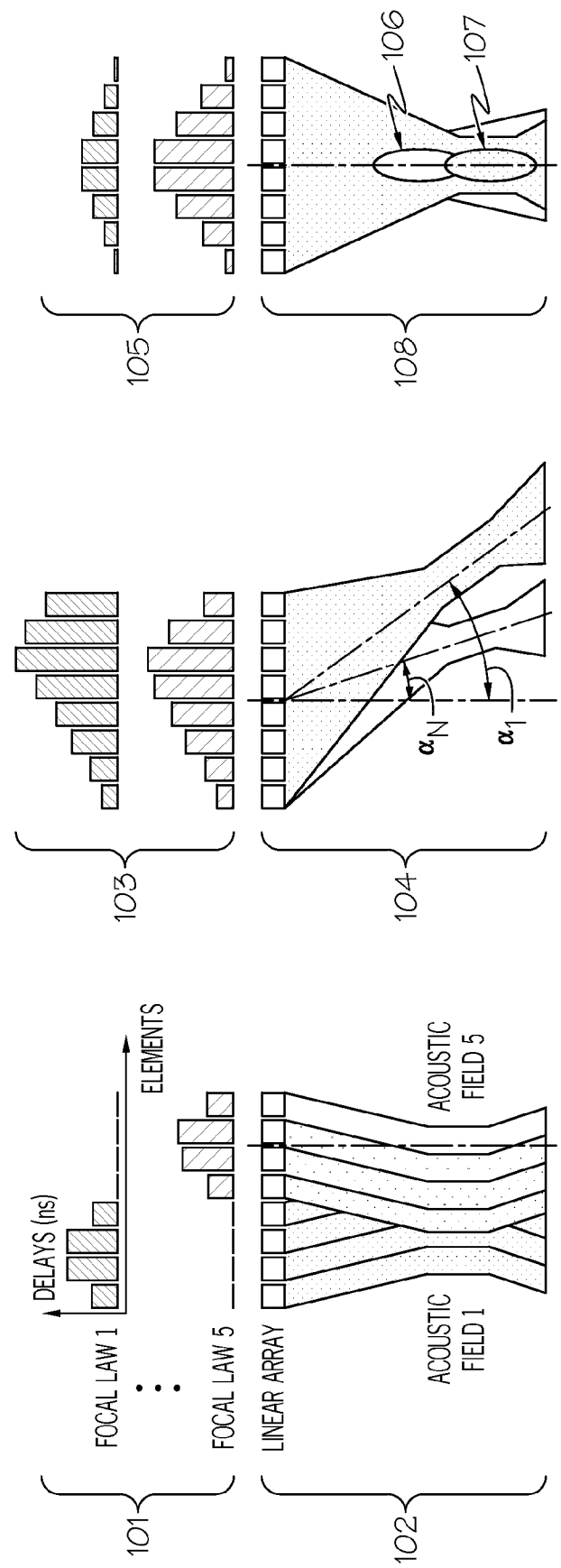
FIGS. 1A through 1C depict exemplary scanning pattern using phased array ultrasonic methods.

The following detailed description is merely exemplary in nature and is not intended to limit the invention or the application and uses of the invention. As used herein, the word "exemplary" means "serving as an example, instance, or illustration." Any embodiment described herein as "exemplary" is not necessarily to be construed as preferred or advantageous over other embodiments. Furthermore, there is no intention to be bound by any theory presented in the preceding background or the following detailed description.

In order to ensure the structural integrity of friction-welded blisks, it is beneficial to employ a monitoring process during manufacturing of the blisks to proactively detect defects such as lack of bonding, cracks, or foreign inclusions. Currently, no conventional NDE methods is capable of inspecting the entire friction-welded region of a blisk due to limited accessibility as a result of their complex geometry. Embodiments of the present disclosure, therefore, are directed to a novel ultrasonic NDE method capable of inspect both subsurface and bulk structures, thereby making sure that no unacceptable anomalies are present in the welded region of the manufactured blisk.

Embodiments of the present disclosure may employ either or both of conventional ultrasonics and phased array ultrasonics. As is known in the art, conventional ultrasonic transducers for NDE commonly include either a single active element that both generates and receives high frequency sound waves, or two paired elements, one for transmitting and one for receiving (T/R). Phased array probes, on the other hand, typically consist of a transducer assembly with from 16 to as many as 256 small individual elements that can each be pulsed separately. These may be arranged in a strip (linear array), a ring (annular array), a circular matrix (circular array), or a more complex shape.

As is the case with conventional transducers, phased array probes may be designed for direct contact use, as part of an angle beam assembly with a wedge, or for immersion use with sound coupling through a water path. Transducer frequencies are most commonly in the range from 2 MHz to 20 MHz. A phased array system will also include a computer-based instrument that is capable of driving the multi-element probe, receiving and digitizing the returning echoes, and plotting that echo information in various standard formats. Unlike conventional ultrasonics, phased array systems can sweep a sound beam through a range of refracted angles or along a linear path, or dynamically focus at a number of different depths, thus increasing both flexibility and capability in inspection setups.

A phased array system utilizes the wave physics principle of phasing, varying the time between a series of outgoing ultrasonic pulses in such a way that the individual wave fronts generated by each element in the array combine with each other to add or cancel energy in predictable ways that effectively steer and shape the sound beam. This is accomplished by pulsing the individual probe elements at slightly different times. Frequently the elements will be pulsed in groups of 4 to 32 in order to improve effective sensitivity by increasing aperture, which reduces unwanted beam spreading and enables sharper focusing.

Software known as a focal law calculator establishes specific delay times for firing each group of elements in order to generate the desired beam shape, taking into account probe and wedge characteristics as well as the geometry and acoustical properties of the test material. The programmed pulsing sequence selected by the instrument's operating software then launches a number of individual wave fronts in the test material. These wave fronts in turn combine constructively and destructively into a single primary wave front that travels through the test material and reflects off cracks, discontinuities, back walls, and other material boundaries like any conventional ultrasonic wave. The beam can be dynamically steered through various angles, focal distances, and focal spot sizes in such a way that a single probe assembly is capable of examining the test material across a range of different perspectives. This beam steering happens very quickly, so that a scan from multiple angles or with multiple focal depths can be performed in a small fraction of a second.

Exemplary scanning patterns are depicted in FIGS. 1A-1C. For example, FIG. 1A depicts a linear scan 101 and the resulting acoustic fields 102. FIG. 1B depicts a sectorial scan 103 and the resulting acoustic fields 104. Further, FIG. 1C depicts a depth focusing scan 105, with two different beam depths 106, 107 shown (of course, any number of depths may be scanned), and the resulting acoustic field 108.

The returning echoes are received by the various elements or groups of elements and time-shifted as necessary to compensate for varying wedge delays and then summed Unlike a conventional single element transducer, which will effectively merge the effects of all beam components that strike its area, a phased array transducer can spatially sort the returning wavefront according to the arrival time and amplitude at each element. When processed by instrument software, each returned focal law represents the reflection from a particular angular component of the beam, a particular point along a linear path, and/or a reflection from a particular focal depth. The echo information can then be displayed in any of several formats known in the art.

Figure 2:
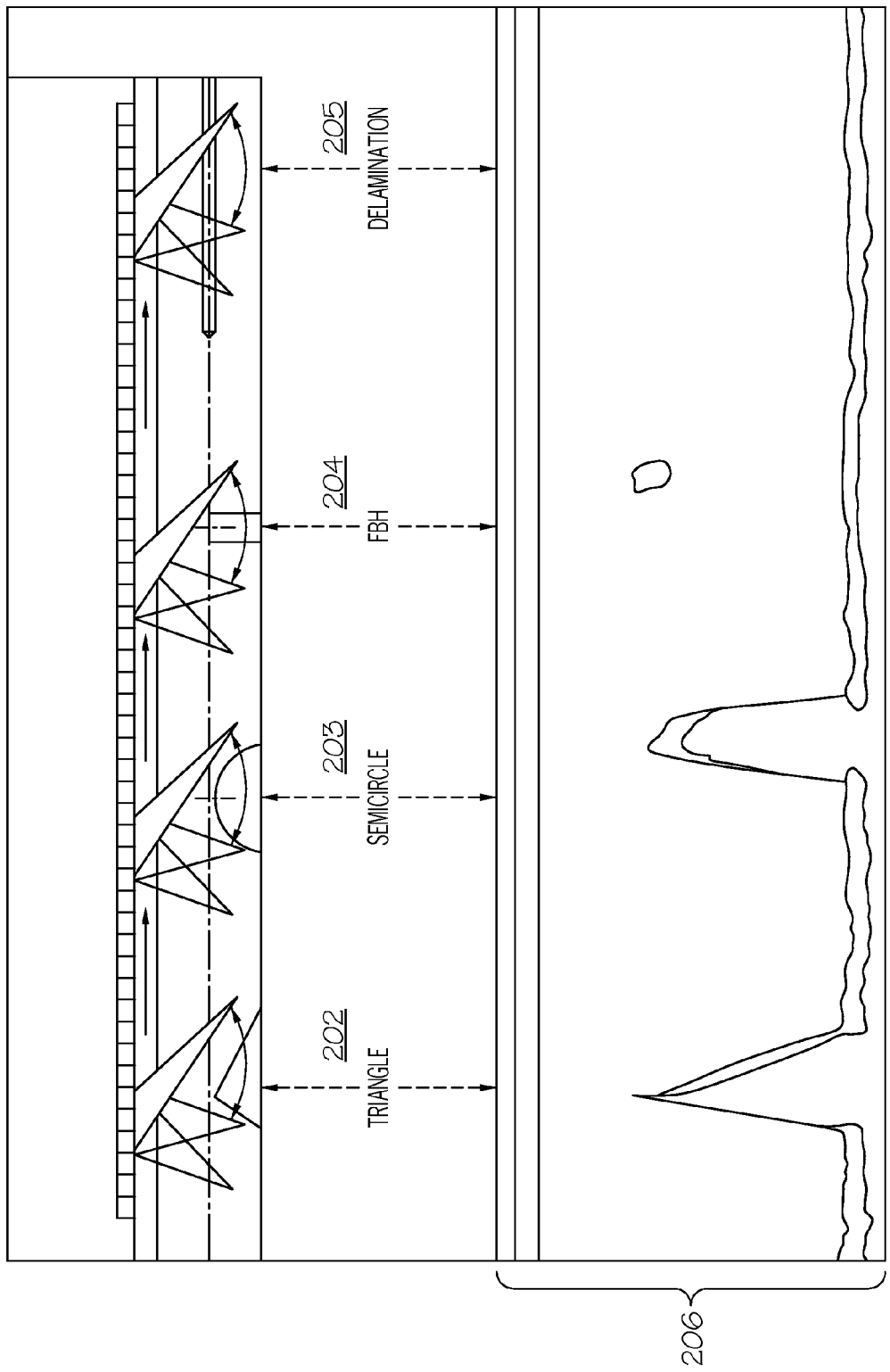
FIG. 2 depicts an exemplary C-scan image produced using phased array ultrasonic methods.

For example, a "C-Scan" is a two dimensional presentation of data displayed as a top or planar view of a test piece, similar in its graphic perspective to an x-ray image, where color represents the gated signal amplitude at each point in the test piece mapped to its x-y position. With conventional instruments, the single-element transducer must be moved in an x-y raster scan pattern over the test piece. With phased array systems, the probe is typically moved physically along one axis while the beam electronically scans along the other. Encoders will normally be used whenever precise geometrical correspondence of the scan image to the part must be maintained, although un-encoded manual scans can also provide useful information in many cases. An exemplary C-scan image is depicted in FIG. 2, as might result from the scan of an exemplary substrate. FIG. 2 shows a scanning procedure directed at four shaped defects 202 (triangle), 203 (semi-circle), 204 (FBH—flat bottom holes), and 205 (delamination) in a sample substrate. For example, horizontally polarized shear waves are very sensitive to any cracks or delamination. Skimming waves may also be optionally employed to detect other defects. The returning wavefront images from scanning the shaped defects 202-205 are correspondingly depicted at 206.

Figure 3A:
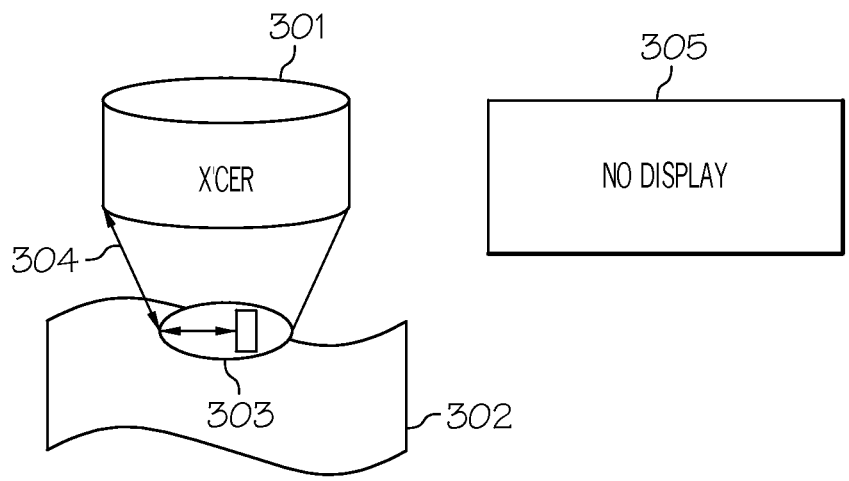
FIGS. 3A and 3B depict an exemplary ultrasonic scanning procedure.
Figure 3B:
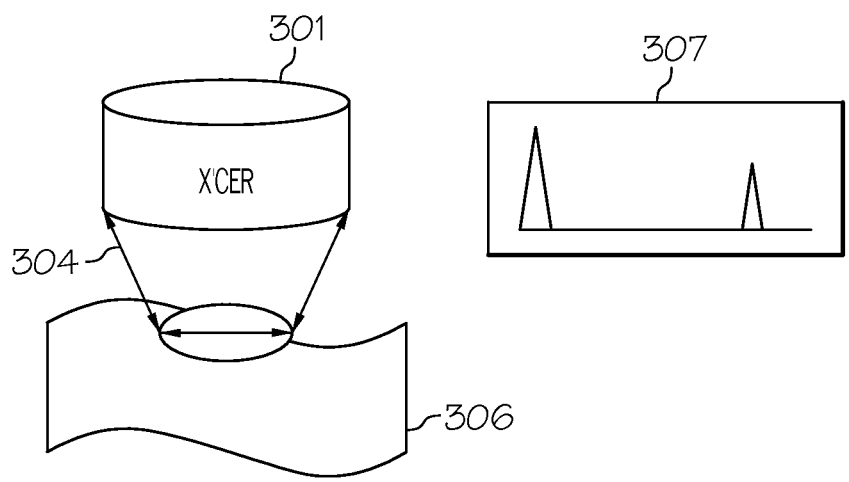

Detection of defects using ultrasonics can, in one embodiment, be based on the "leaky wave" principle. As shown with regard to FIG. 3A, a transducer 301 can be configured to scan a substrate 302, that includes an anomaly (i.e., a defect) 303 therein. As indicated by the arrow 304, the "leaky" wave 304 does not pass through the anomaly 303, and no leaky wave is detected (the absence thereof being indicated by reference numeral 305), resulting in no display. In contrast, with regard to FIG. 3B, wherein the transducer 301 is configured to scan a substrate 306 that does not include an anomaly therein. As shown, wave 304 passes through to be detected, as indicated by reference numeral 307, and the detected pattern is displayed.

The benefits of phased array technology over conventional ultrasonics come from its ability to use multiple elements to steer, focus and scan beams with a single transducer assembly. Beam steering, commonly referred to sectorial scanning, can be used for mapping components at appropriate angles. Electronic focusing permits optimizing the beam shape and size at the expected defect location, thus further optimizing probability of detection. The ability to focus at multiple depths also improves the ability for sizing critical defects for volumetric inspections. Focusing can significantly improve signal-to-noise ratio in challenging applications, and electronic scanning across many groups of elements allows for scan images to be produced very rapidly.

Figure 4A:
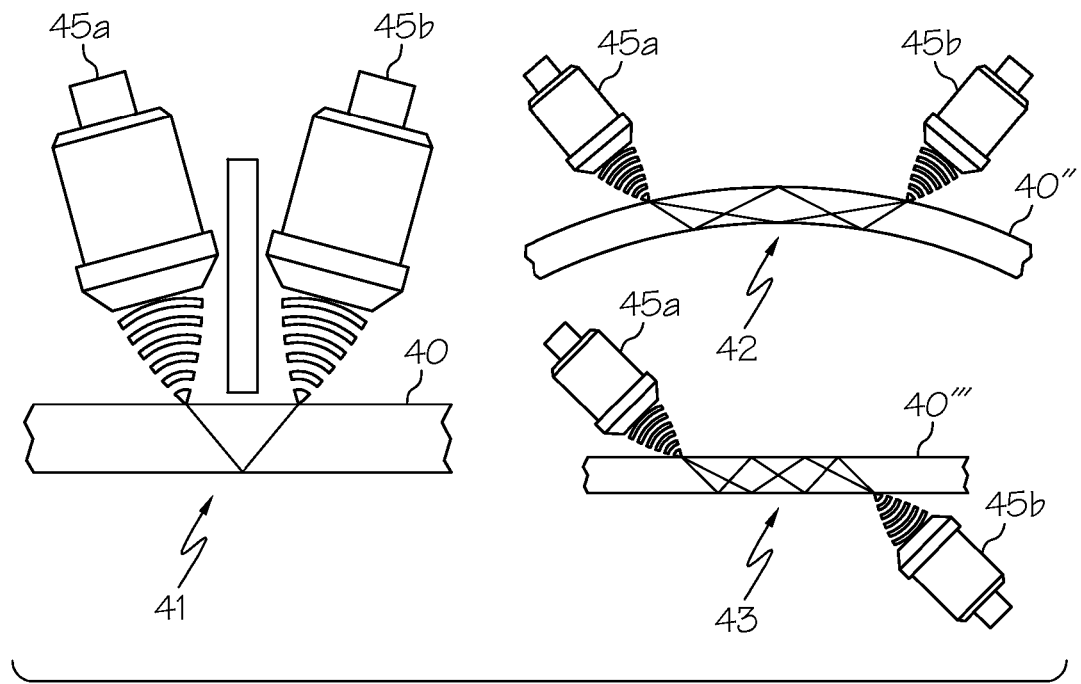
FIGS. 4A through 4C depict exemplary transducer/receiving scanning configurations suitable for use with embodiments of the present disclosure.
Figure 4B:
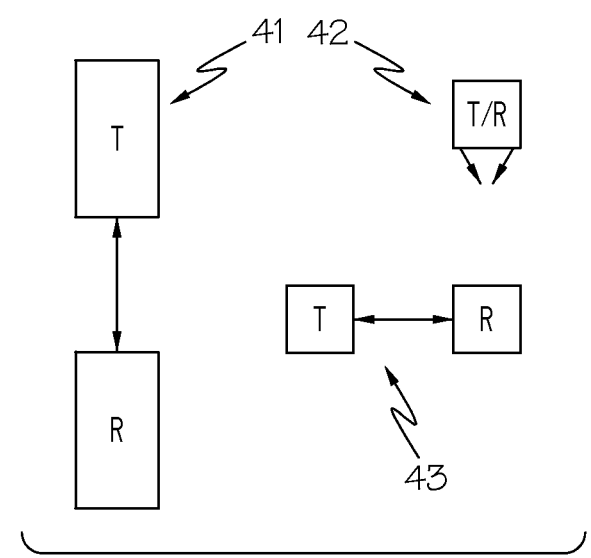
Figure 4C:
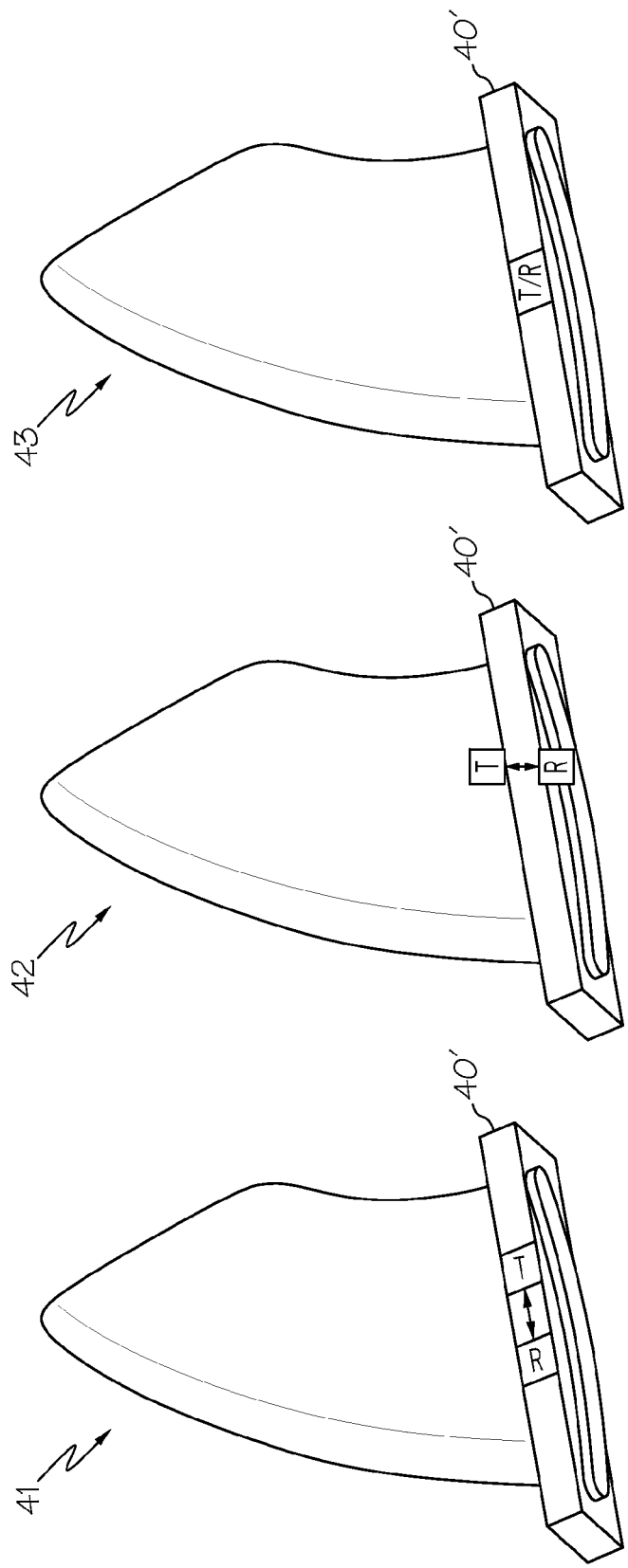

Referring now to FIGS. 4A, 4B, and 4C various transducer/receiver ("T/R") configurations are depicted as may be employed in connection with some embodiments of the present disclosure. For each configuration, a schematic (FIG. 4A) of the T/R devices 45a/45b, respectively, is depicted in a scanning position over a substrate 40, which could be the welded region of a blisk. Also for each configuration, a relational diagram (FIG. 4B) of the T/R configuration is also depicted. Still further, for each configuration, a schematic (FIG. 4A) of the T/R devices 45a/45b, respectively, is depicted in a scanning position over an exemplary portion of blisk substrate 40' (including the welding region around a single blade of the blisk). For example, for each of FIGS. 4A and 4B, reference numeral 41 depicts the T/R configuration over the substrate 40 in a circumferential configuration. In this configuration, using the transmitter and receiver along and perpendicular to radial directions will enable inspection for detecting anomalies either lying along circumference or perpendicular to it. Reference numeral 42 depicts the T/R configuration over the substrate 40 in a radial direction configuration. Further, reference numeral 43 depicts the T/R configuration over the substrate 40 in a lateral or radial configuration. It will be appreciated that the configurations 41-43 are presented merely for exemplary purposes. One having ordinary skill in the art will be able to employ alternate configurations adapted to the shape of the substrate being scanned, in accordance with the teachings of the present disclosure.

Figure 5A:
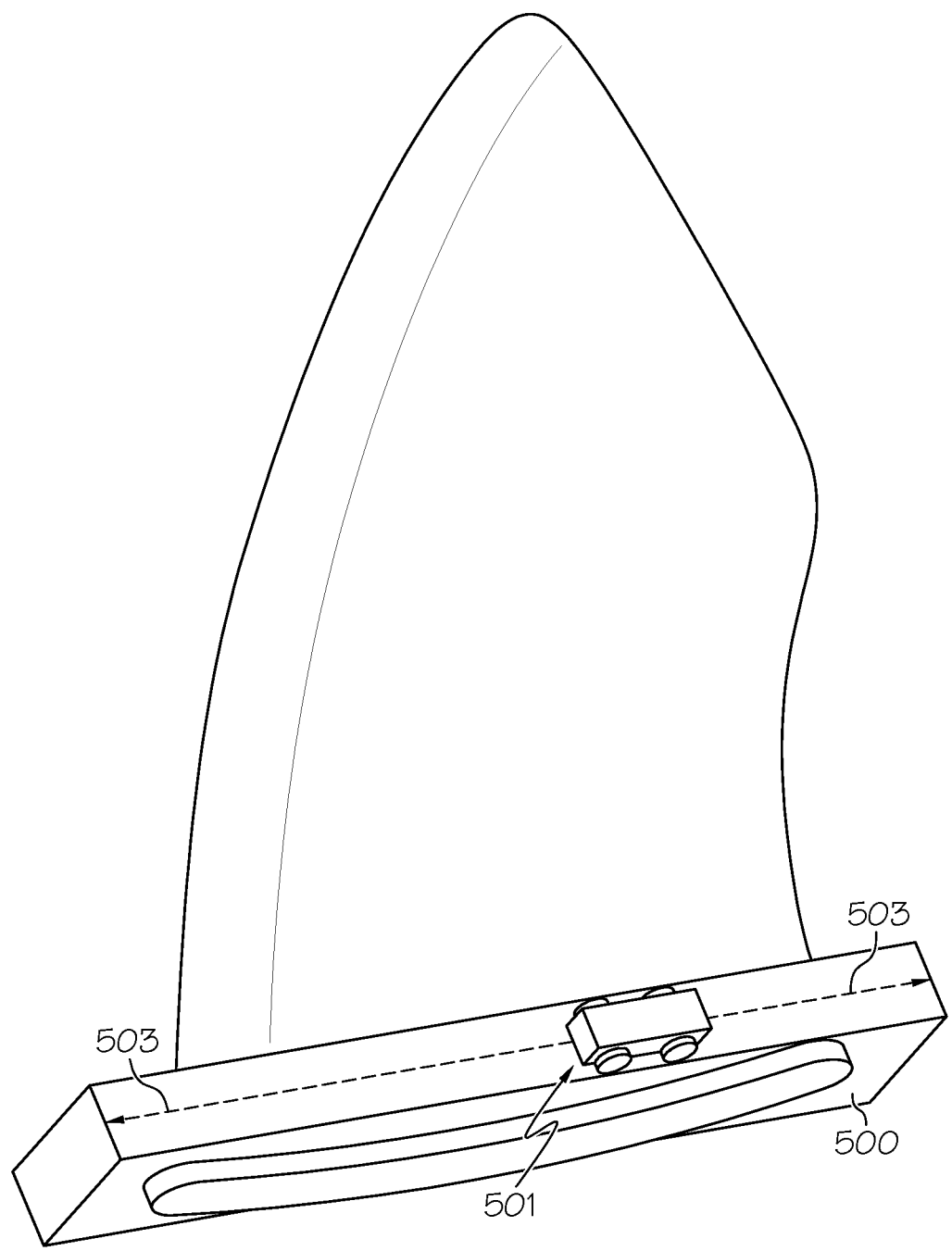
FIGS. 5A and 5B depicts an exemplary moving transducer/receiver configuration.
Figure 5B:
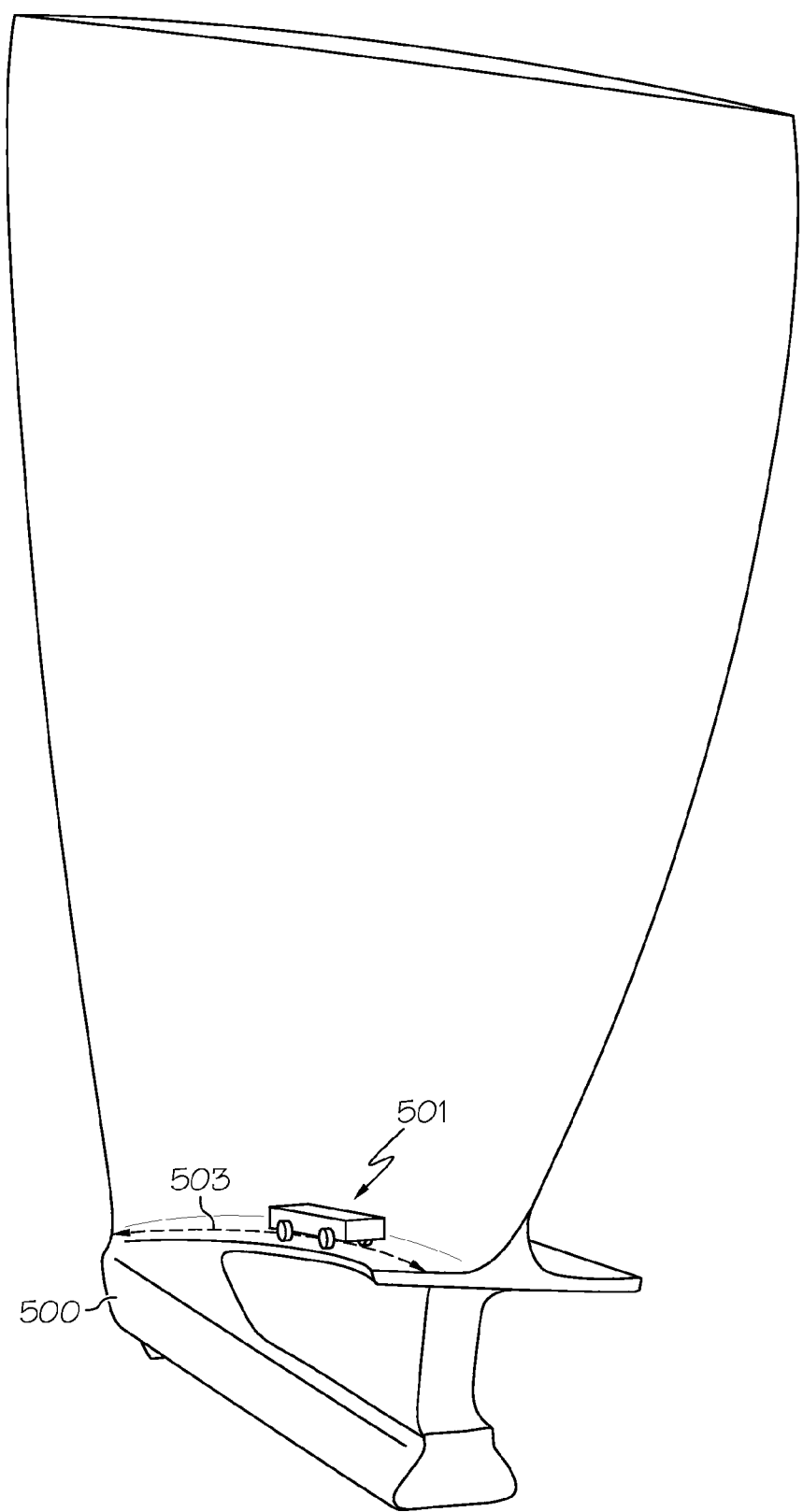

In a particular embodiment, depicted in FIG. 5A, the T/R devices may be configured in the form of a moving (or "crawling") transducer ("crawler") device 501 deployed on a substrate 500a, such as a welding block portion of a blisk as shown in FIG. 5A. In another exemplary embodiment, depicted in FIG. 5B (which is a cut-away view of a single blade on a blisk), the T/R devices may be deployed above a hub portion 500b on a finished airfoil section. In general, crawler device 501 can be implemented as any automated component that can move in at least one direction (movement indicated in two directions in FIGS. 5A and 5B by arrows 503), and that can be programmed to move over a pre-determined course, the pre-determined course being anywhere along the blisk that is may be desired to perform NDE. For example, crawler device can be configured to automatically move over a given region of interest (ROI) on a blisk. Again, the region of interest generally can be anywhere on the blisk, but as particularly shown in FIG. 5A it is along the welding block and as particularly shown in FIG. 5B it is along a finished airfoil. FIGS. 5A and 5B are therefore not intended to be limiting as to the region or manner where device 501 may operate. The crawler device 501 includes T/R devices built therein. As such, as the crawler device 501 automatically moves over the substrate 500a,b, ultrasonic waves can be sent and received by the crawler in any of the manner discussed above for detecting anomalies in the substrate 500a,b. Crawler 501 can be cordless, and include a power source therewithin. Alternatively, it may be coupled to a power source.

Crawler 501 can include data storage and/or transmission components, as are known in the art, for storing the ultrasonic scans thereon, or transmitting them to a receiver located elsewhere for contemporaneous evaluation of the substrate 500a,b as it is scanned. It has been discovered that crawlers are a particularly useful T/R scanning implementation means for blisks due to their automated nature (i.e., they can be placed on the blisk, and left to perform the scan without further intervention by an operator) and due to their configurability (i.e., they can be sized to fit between blades of a blisk for scanning the welding therebetween, areas that are otherwise difficult to access and scan using conventional T/R devices).

Figure 6A:
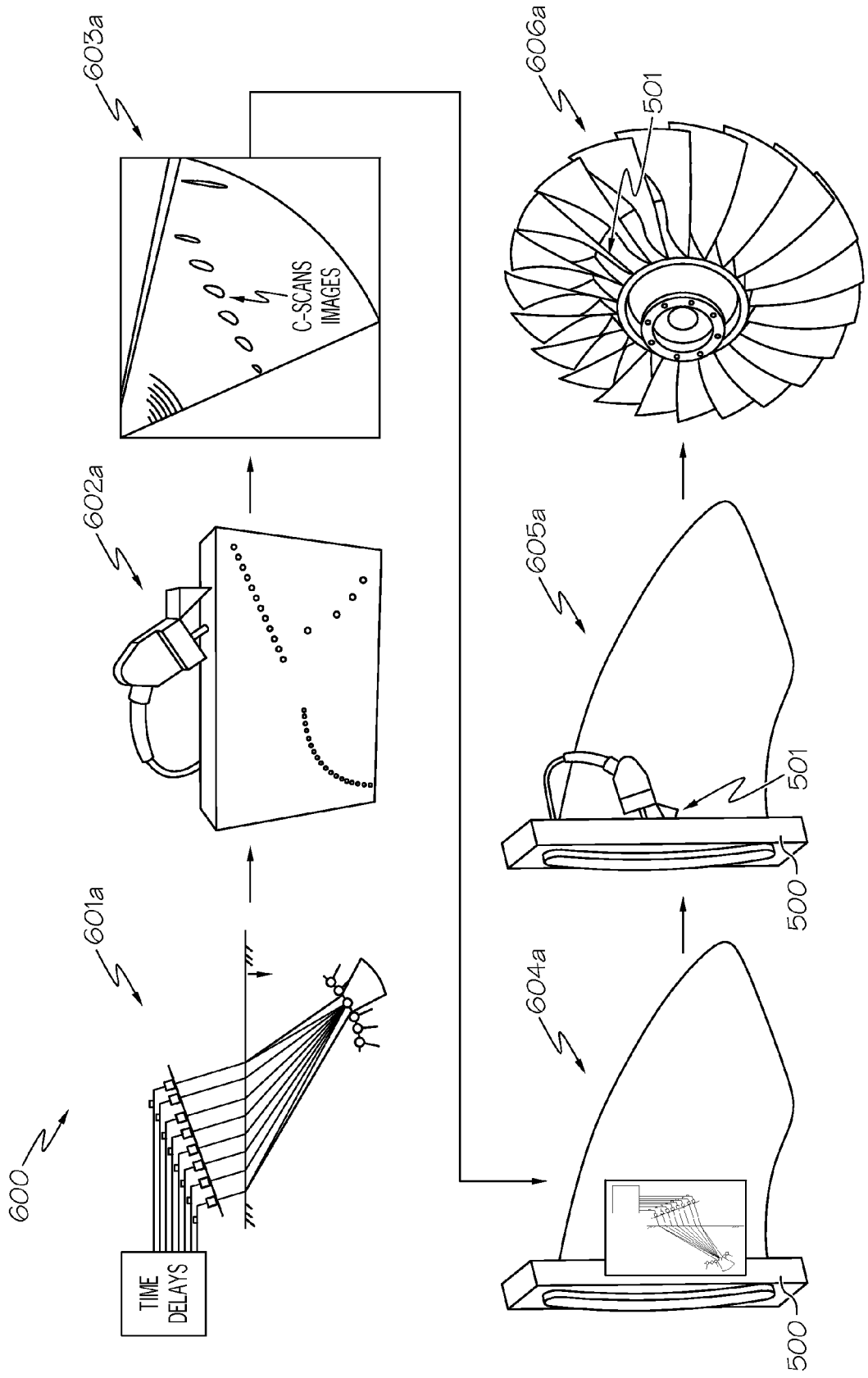
FIGS. 6A through 6C are illustrative of an exemplary method in accordance with the present disclosure.
Figure 6B:
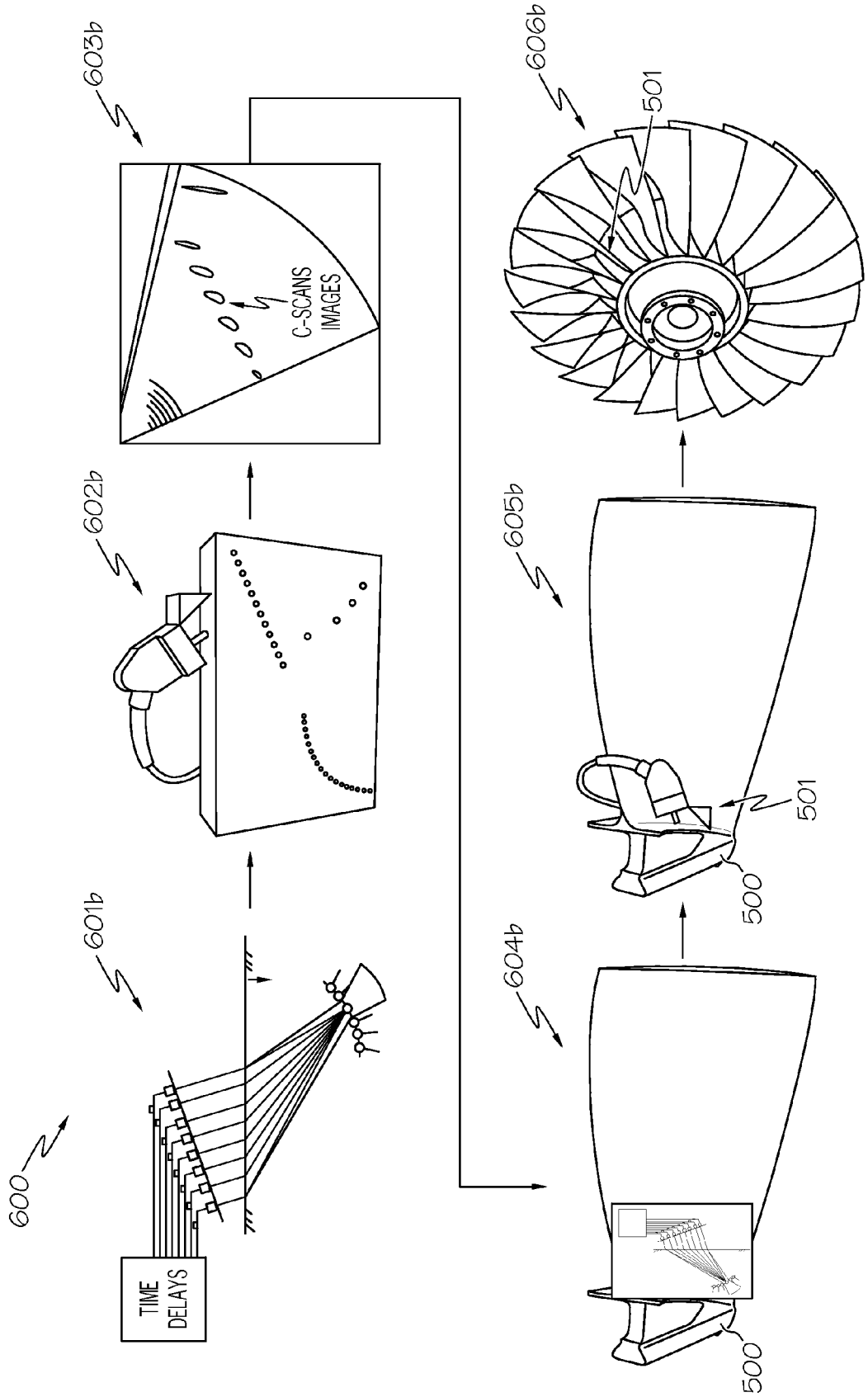
Figure 6C:
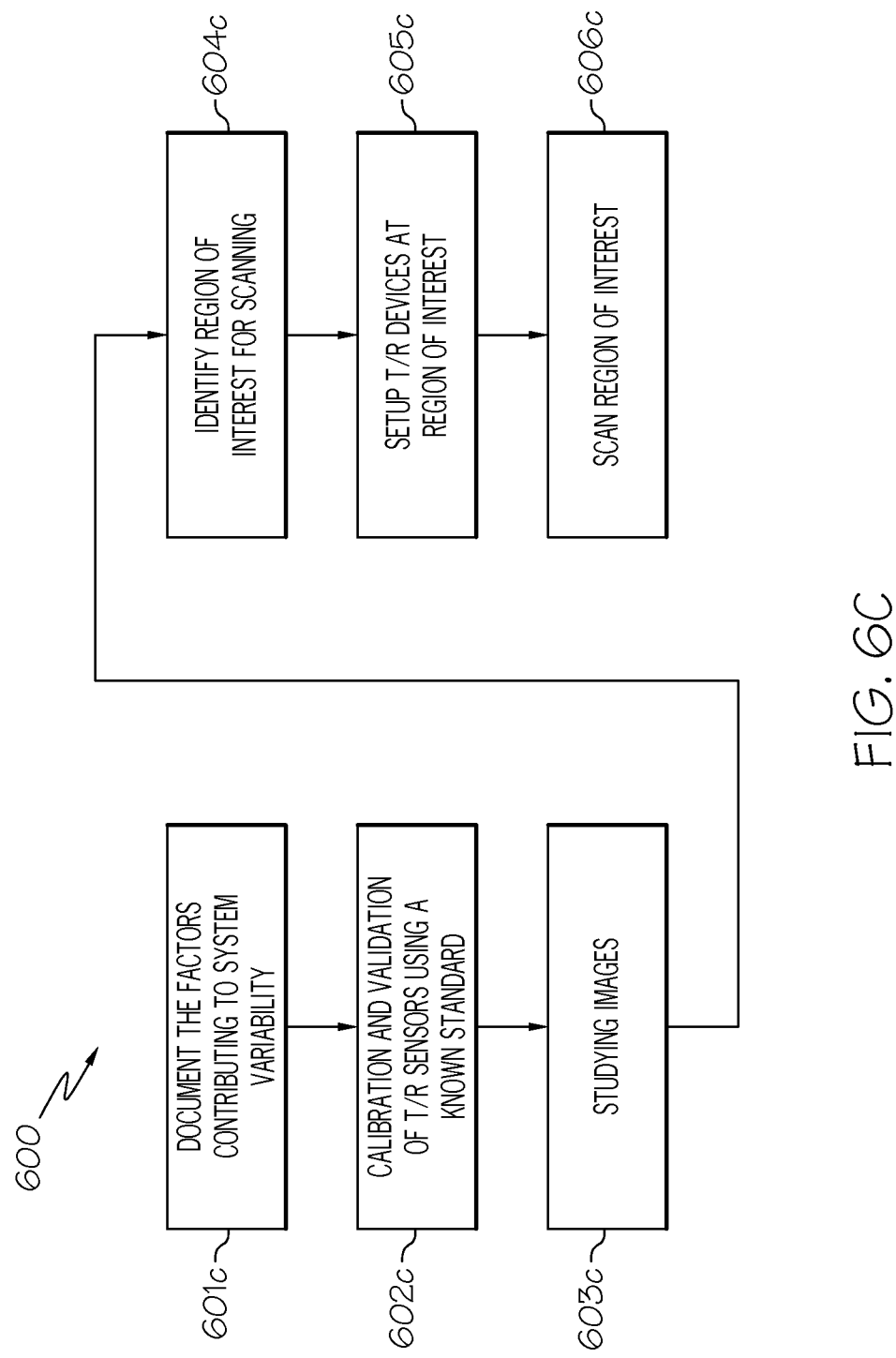

In one embodiment, an exemplary method 600 for performing NDE using ultrasonics on a welded blisk is described with regard to FIGS. 6A through 6B. In particular, FIGS. 6A and 6B illustrates various images representing the method steps (with regard to the embodiment of a welding block configuration and with regard to a finished airfoil configuration, respectively), and FIG. 6C illustrates the method steps using a flow diagram. In an embodiment, the exemplary method 600 includes documenting factors contributing to variability in the system to be scanned (601a-c). Variability can include, among other things, the angle of scanning, the focal planes of scanning, the shape of the object to be scanned, and the type of scanning to be performed, among others. In an embodiment, the exemplary method 600 includes calibrating and validating the T/R devices using a known, standard substrate (602*a-c*). For example, the T/R sensors can scan a known blisk device that does not have any defects to determine a reference image with which to compare scans of newly manufactured blisks during an NDE process. In an embodiment, the exemplary method 600 includes studying the resulting scan images, for example C-scan images, to determine expected patterns (603*a-c*).

Furthermore, the exemplary method 600 includes identifying a region of interest on a substrate, for example the friction-welded region of a blisk (604*a-c*). Still further, the exemplary method 600 includes the setup of a T/R device in the identified region of interest (605*a-c*). For example, as noted above, setup can include deploying one or more crawler devices for automatically and without human intervention scanning the region of interest using ultrasonic methods. Conventional T/R devices can be employed additionally or alternatively. In an embodiment, the method 600 further includes scanning the region of interest. As discussed above, various ultrasonic methods and techniques can be employed in this step. As shown in FIGS. 6A and 6B, at image 606*a* and image 606*b*, a crawler device has be employed and is traversing a region of interest on the blisk while scanning using ultrasonics. Data can be collected by the crawler, and/or contemporaneously transmitted to an operator for viewing.

In a variation of this embodiment, scanning the region of interest may be accomplished using electromagnetic acoustic transducers (EMATs) using transmitters and receivers to produce the scan image. In yet another variation of this embodiment, scanning the region of interest may be accomplished using LASER assisted ultrasonic (LAUT) techniques using an appropriate LASER source as a transmitter and air-coupled PZT or optical sensors as receivers to produce the scan image. In still another variation of this embodiment, scanning the region of interest may be accomplished using a non-linear ultrasonic driver and using several receivers for receiving several multiple harmonics for analyzing structural integrity, and producing a scan image thereby. In still another variation of this embodiment, the method may further include, with regard to any of the above scanning modalities, identifying the interfaces joining the blades and the disk, and a grain size distribution in the region of interest. For example, in one embodiment, EMAT and LAUT can be used for welding process monitoring during a linear friction welding process to identify any process introduced anomalies.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It is being understood that various changes may be made in the function and arrangement of elements described in an exemplary embodiment without departing from the scope of the invention as set forth in the appended claims.

What is claimed is:

1. A method for non-destructive evaluation of a bladed disc structure comprising an central, annular hub and a plurality of blades extending from the annular hub, the method comprising:
    identifying a plurality of regions of interest on the bladed disc structure, wherein the plurality of regions of interest comprise areas of the bladed disc structure that have been friction welded, wherein the plurality of regions of interest include an area or volume of the bladed disc structure between a positioned ultrasonic transducer and receiver, and wherein the plurality of regions of interest include at least 1) a first region between the transducer and the receiver when both the transducer and receiver are placed along a circumferential perimeter of the annular hub adjacent to one of the plurality of blades and 2) a second region that extends radially between a hub inner surface and a hub outer surface adjacent to one of the plurality of blades;
    positioning the ultrasonic transducer and receiver in the plurality of regions of interest, wherein the transducer and comprises a crawling device that is in direct physical contact with the bladed disc structure and that moves along the bladed disc structure in the plurality of regions of interest in an automated, pre-programmed manner without intervention from an operator, and wherein the crawling device is sized so as to be able to fit between adjacent blades of the plurality of blades extending from the annular hub;
    scanning the plurality of region of interest using the ultrasonic transducer and receiver to produce a scan image, wherein scanning comprises the crawling device moving in direct physical contact with the bladed disc structure in the plurality of regions of interest in the automated, pre-programmed manner without intervention from the operator; and
    comparing the scan image against a reference image to determine the presence of an anomaly in the region of interest, wherein comparing comprises determining the presence of at least one difference between the scan image and the reference image, the at least one difference being indicative of an anomaly.

2. The method of claim 1, wherein positioning the ultrasonic transducer and receiver comprises positioning a single ultrasonic transducer and receiver.

3. The method of claim 1, wherein positioning the ultrasonic transducer and receiver comprises positioning a phased-array ultrasonic (PAUT) transducer and receiver.

4. The method of claim 1, further comprising scanning a reference structure using an ultrasonic transducer and receiver to produce the reference image.

5. The method of claim 1, wherein scanning the region of interest comprises circumferentially scanning the region of interest.

6. The method of claim 1, wherein scanning the region of interest comprises detecting a leaky wave.

7. The method of claim 1, wherein scanning the region of interest using the ultrasonic transducer and receiver comprises generating and detecting an ultrasonic wave from the moving ultrasonic transducer and receiver.

8. The method of claim 1, further comprising storing the scan image.

9. The method of claim 1, further comprising transmitting the scan image.

10. The method of claim 9, wherein scanning the region of interest and comparing the scan image are performed contemporaneously.

* * * * *